(12) United States Patent
Elgas et al.

(10) Patent No.: US 6,579,257 B1  
(45) Date of Patent: Jun. 17, 2003

(54) AUTOMATED OCCLUSION CLAMP FOR CENTRIFUGAL BLOOD PUMPS

(75) Inventors: Roger J. Elgas, Anaheim Hills, CA (US); Michael P. Petersen, Eden Prairie, MN (US)

(73) Assignee: Medtronic, Inc., Brooklyn Park, MN (US)

( * ) Notice: Subject to any disclaimer, the term of this patent is extended or adjusted under 35 U.S.C. 154(b) by 0 days.

(21) Appl. No.: 09/400,135

(22) Filed: Sep. 21, 1999

(51) Int. Cl.[7] ............................................. A61M 31/00
(52) U.S. Cl. ....................................................... 604/67
(58) Field of Search ............................... 604/6.11, 6.15, 604/246, 247, 250

(56) References Cited

U.S. PATENT DOCUMENTS

| | | | | |
|---|---|---|---|---|
| 5,154,704 A | * | 10/1992 | Archibald | 604/250 |
| 5,215,450 A | * | 6/1993 | Tamari | 417/474 |
| 5,318,515 A | * | 6/1994 | Wilk | 604/250 X |
| 5,980,465 A | * | 11/1999 | Elgas | 604/6.11 X |

* cited by examiner

Primary Examiner—Manuel Mendez  
(74) Attorney, Agent, or Firm—Stout, Uxa, Buyan & Mullins, LLP; Donald E. Stout

(57) ABSTRACT

Retrograde flow in an extracorporeal blood circuit using a centrifugal blood pump is prevented by passing the blood line through a normally-closed powered occlusion clamp, and opening the clamp in response to powering of the pump or, preferably, in response to the sensing of forward blood flow in the extracorporeal circuit.

8 Claims, 2 Drawing Sheets

AUTOMATED OCCLUSION CLAMP FOR CENTRIFUGAL BLOOD PUMPS

FIELD OF THE INVENTION

This invention relates to heart-lung machines, and more particularly to an automatic occlusion clamp that prevents retrograde blood flow through a centrifugal blood pump.

BACKGROUND OF THE INVENTION

In a typical heart-lung machine of the type used in open-heart surgery, an extracorporeal blood circuit is established from the patient's venous system through a venous reservoir, a blood pump and an oxygenator to the patient's arterial system. This circuit takes over the function of the patient's heart and lungs while the patient's heart is stopped for the surgery.

The blood pump in the extracorporeal circuit is typically either a roller pump or a centrifugal pump. An advantage of the roller pump is that the blood line is always occluded at some point in the pump, so that there can be no retrograde blood flow in the circuit when the pump is stopped. A disadvantage is that a roller pump can convey air boluses through the line. Such air boluses need to be dealt with separately in order to avoid serious injury or death of the patient.

Centrifugal pumps, on the other hand, do not convey air boluses through the circuit. If an air bolus is applied to the intake of a centrifugal pump, the pump deprimes and needs to be reprimed and restarted. Because of this safety factor, centrifugal pumps are the preferred choice of many perfusionists.

A problem with centrifugal pumps is that they do not occlude the line, and that consequently, retrograde blood flow through the pump is possible when the pump is stopped, due to the pressure head in the patient's arterial system. Such a retrograde flow drains blood from the patient and is medically unacceptable.

Retrograde flow through a centrifugal pump has been averted in the prior art by inserting into the extracorporeal circuit a one-way duckbill valve. The use of such a valve, though effective, does have two disadvantages: first, the shape of a duckbill valve causes turbulence at the exit end of the valve and thereby causes some hemolysis; and second, the duckbill valve, because it is part of the extracorporeal circuit, is a single-use item and therefore adds to the cost of patient disposables.

SUMMARY OF THE INVENTION

The present invention overcomes the above-described deficiencies of the prior art by providing an electrically or pneumatically operated occlusion clamp external to the blood line that is arranged to occlude the line, preferably between the centrifugal pump and the oxygenator, whenever the forward blood flow in the line essentially ceases. The clamp of this invention is designed to operate in a fail-safe mode, i.e. it will clamp the line shut in the event of a power failure. In combination with conventional devices that shut down the pump in the event of a low blood level condition in the venous reservoir and/or of the detection of an air bolus, the present invention provides a triple-action safety system.

DESCRIPTION OF THE PREFERRED EMBODIMENT

Figure 1:
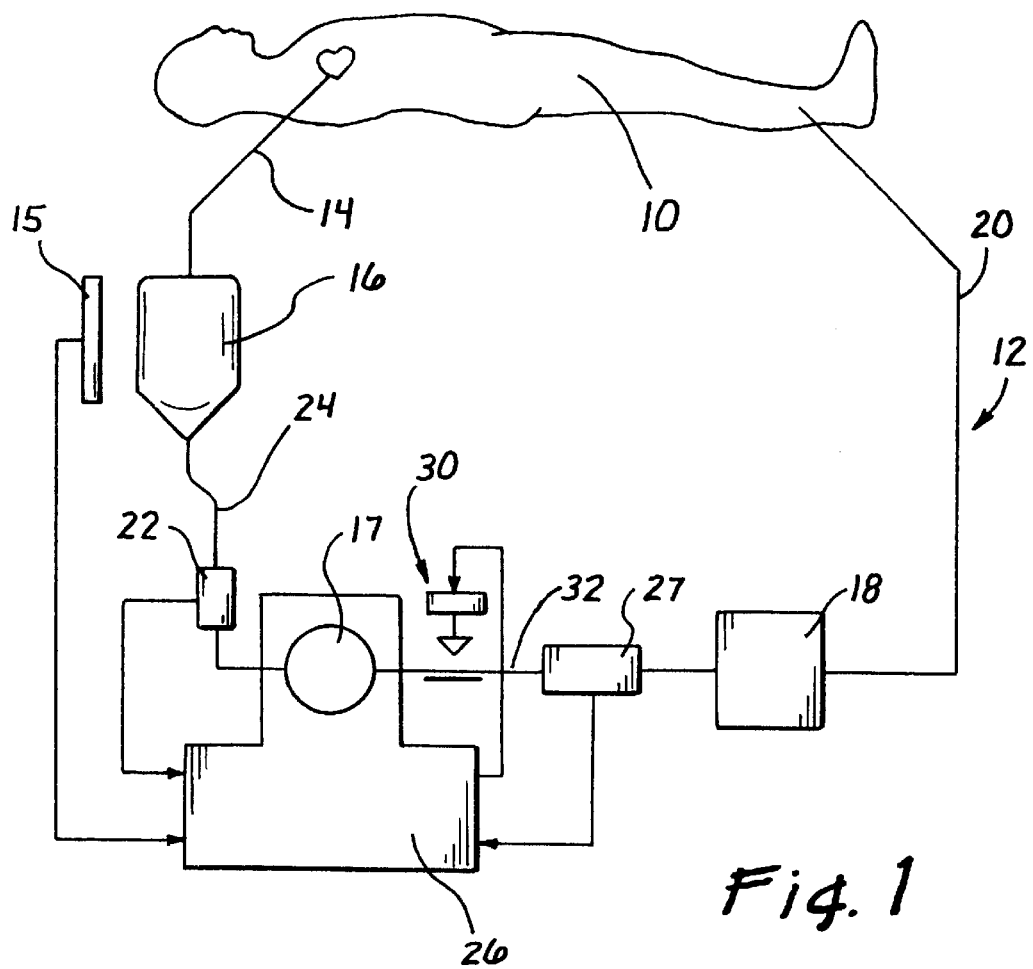
FIG. 1 is a block diagram of an extracorporeal circuit using the invention.

FIG. 1 illustrates the environment in which the invention is useful. A patient 10 undergoing open heart surgery is connected to the extracorporeal circuit 12 by a venous line 14 which discharges venous blood by gravity into a venous reservoir 16. Filtered and defoamed cardiotomy blood may also be introduced into the reservoir 16 by appropriate equipment (not shown). The venous reservoir 16 may be equipped with a conventional level sensor 15.

Blood is pumped by a pump 17 from the venous reservoir 16 into the oxygenator 18 and the arterial line 20 connected to the patient 10. A conventional air sensor 22 may be connected in the line 24 between the reservoir 16 and the pump 17. The level sensor 15 and the air sensor 22 provide conventional inputs to the perfusionist's control console 26. A conventional flow sensor 27 preferably connected between the pump 17 and the oxygenator 18 also provides an input to the console 26.

Although the blood pump 17 may be of any suitable type, the present invention is useful specifically with centrifugal pumps. These pumps have certain advantages that make them desirable in extracorporeal blood circuits, but they permit retrograde blood flow through the pump when the pump is stopped, and they can be deprimed by an air bolus in the blood line.

A problem thus arises when a centrifugal pump 17 is stopped during open-heart surgery. This occurs from time to time, for example when the surgeon wants to stop blood flow into the surgical field for a few seconds to enhance visibility. At such times, the pressure head of about 200–300 mmHg in the patient's arterial system drives oxygenated blood backward through the extracorporeal circuit 12 unless it is restrained from doing so.

With a roller pump, this restraint is automatic because a roller pump inherently occludes the line when it is stopped. With a centrifugal pump, the prior art typically restrained retrograde blood flow by inserting a one-way valve, such as a duckbill valve, in the extracorporeal line between the pump 17 and the oxygenator 18. The disadvantage of this approach was, first, that the valve, being part of the blood path in the extracorporeal circuit 12, had to be disposable; and second, that the valve created turbulence at its outlet and thereby caused some hemolysis.

Figure 3:
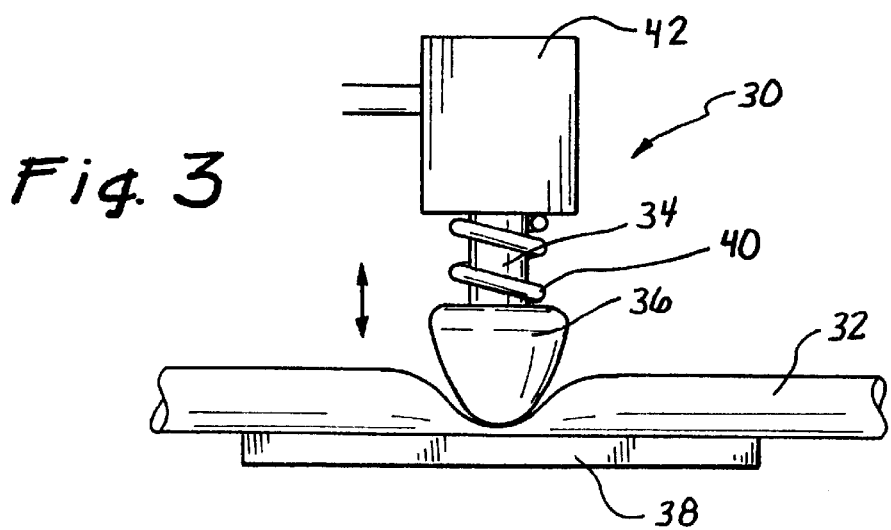
FIG. 3 is a schematic diagram of the clamp of this invention.

In accordance with the invention, the in-line duckbill valve of the prior art is replaced by a mechanical clamp 30 external of the flexible tubing which constitutes the blood line 32. The clamp 30, when actuated, is arranged to pinch or clamp the line 32 so as to preclude blood flow therethrough. The clamp 30, shown in more detail in FIG. 3, is preferably operated electrically but may be operated hydraulically or pneumatically. As shown in FIG. 3, the clamp 30 basically consists of a plunger 34 which carries a clamping head 36. The clamping head 36 is biased toward a platen 38 by a spring 40. The blood line 32 is positioned between the head 36 and the platen 38, so that the spring 40 biases the head 36 into the position of FIG. 3 in which it occludes the flexible tubing of line 32.

In the preferred embodiment, the plunger 34 is mounted in a solenoid 42 so that the head 36 is lifted off the line 32 whenever the solenoid 42 is energized. The clamp 30 is thus fail-safe in that it occludes the line 32 in the event of a power failure. Also, the positive action of the clamp 30 makes it possible, by appropriate control circuitry, to occlude the line 32 under selectable conditions other than the onset of retrograde blood flow.

Figure 2:
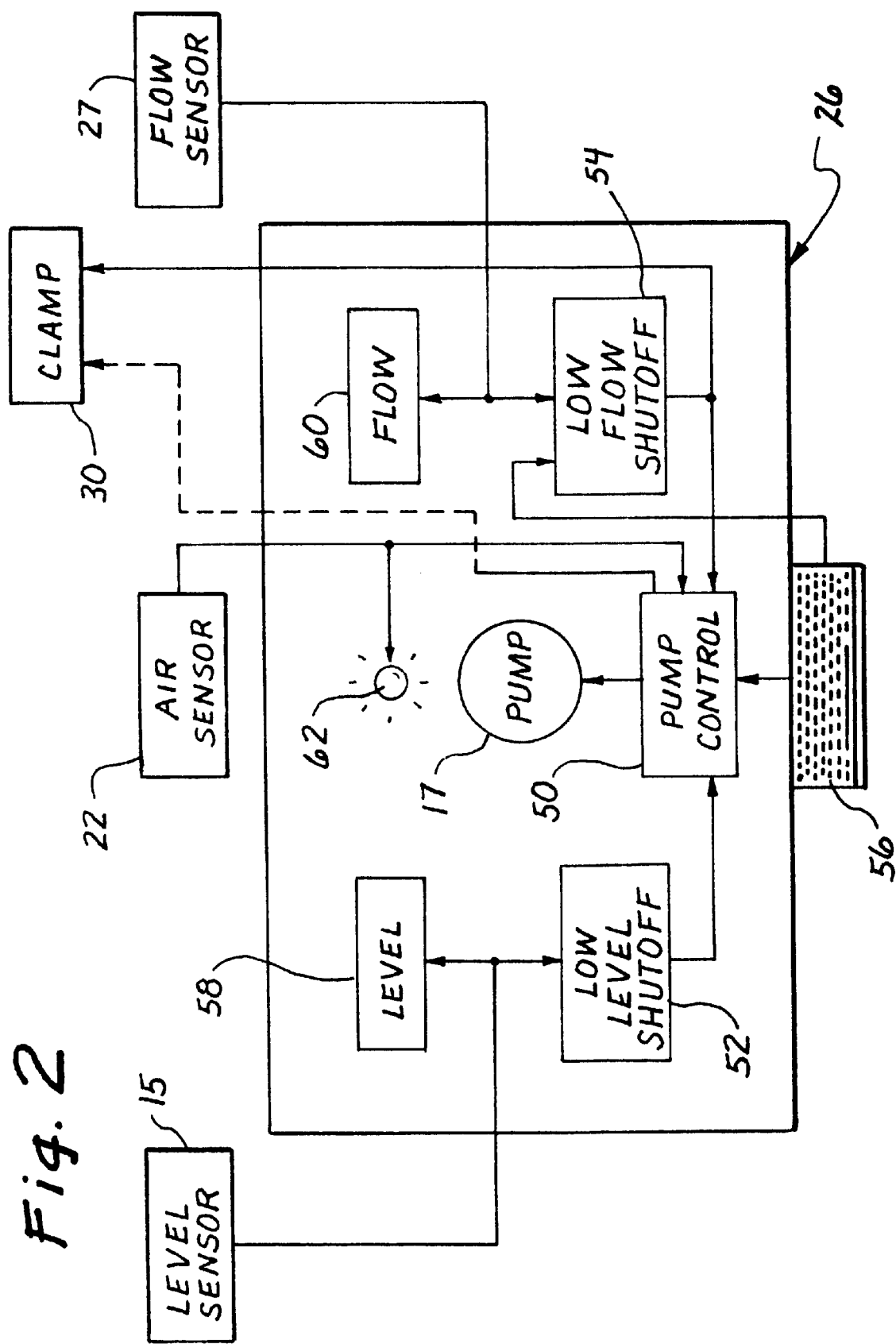
FIG. 2 is a partial block diagram of the perfusionist's console.

The functioning of the inventive apparatus is shown schematically in FIG. 2. The perfusionist's control console 26 contains the pump 17 and a pump control 50 which responds to signals from the low level shutoff circuit 52, the air sensor 22, and the low flow shutoff circuit 54, as well as to manual commands from the operator keyboard 56. A level indicator 58, a flow indicator 60, and an air warning light 62 are provided.

When the pump 17 is to be started, appropriate commands are entered on the keyboard 56. These commands set the pump speed and momentarily override the low flow shutoff circuit 54 so that the pump 17 can start and the clamp 30 releases the blood line 32. As the flow sensor 27 now senses blood flow, the low flow shutoff 54 is deactivated, and the clamp 30 remains retracted and clear of the line 32.

If positive blood flow in the line 32 now ceases, either because the pump 17 has been stopped by the perfusionist or by the action of low level shutoff 52 or air sensor 22, or because a blockage has occurred downstream, the low flow shutoff circuit 54 becomes activated and cuts the power to both the pump (if it is still on) and to the solenoid 42. This causes the clamp head 36 to move against the platen 38 under the action of spring 40. Thus, the line 32 is squeezed between the head 36 and the platen 38, and the line 32 is occluded against retrograde blood flow into the pump 17.

Because the components of clamp 30 are entirely outside of the blood path in line 32, the clamp 30 need not be disposable. Furthermore, while the pump 17 operates, clamp 30 does not constrict nor otherwise affect the flexible line 32, so that the blood path remains clear and free of hemolysis-promoting obstructions.

It is understood that the exemplary automated occlusion clamp for use with centrifugal blood pumps described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

What is claimed is:

1. An extracorporeal blood circuit for heart-lung machines, comprising:
   a) a centrifugal blood pump arranged to pump blood through said circuit;
   b) a line of flexible tubing forming part of said circuit,
   c) a power-actuatable clamping device disposed externally of said line, said device being arranged to normally clamp said line to occlude it, and to release said line for free blood flow therethrough when actuated; and
   d) a flow sensor arranged to produce a signal indicative of blood flow through said line, said clamping device being actuated only as long as said signal indicates forward blood flow through said line.

2. The combination of claim 1, in which said clamping device is spring-biased into line-occluding position, and is power-movable into a line releasing position in response to said signal indicating positive blood flow through said line.

3. The combination of claim 2, in which said clamping device is electrically operated.

4. An extracorporeal blood circuit for heart-lung machines, comprising:
   a) a centrifugal blood pump arranged to pump blood through said circuit;
   b) a line of flexible tubing forming part of said circuit;
   c) a power-actuatable clamping device disposed externally of said line, said device being arranged to normally clamp said line to occlude it, and to release said line for free blood flow therethrough when actuated; and
   d) means for actuating said clamping device when said pump is energized.

5. The extracorporeal blood circuit as recited in claim 1, and further comprising a control console for actuating said clamping device responsive to said signal from said flow sensor.

6. The extracorporeal blood circuit as recited in claim 1, wherein said power-actuatable clamping device comprises a mechanical clamp.

7. The extracorporeal blood circuit as recited in claim 6, wherein said mechanical clamp is solenoid-driven.

8. An extracorporeal blood circuit for heart-lung machines, comprising:
   a) a centrifugal blood pump arranged to pump blood through said circuit,
   b) a line of flexible tubing forming part of said circuit;
   c) a power-actuatable clamping device disposed externally of said line, said device being arranged to normally clamp said line to occlude it, and to release said line for free blood flow therethrough when actuated; and
   d) a control console for actuating said clamping device when said pump is energized.

* * * * *